US008216298B2

(12) United States Patent
Wright et al.

(10) Patent No.: US 8,216,298 B2
(45) Date of Patent: Jul. 10, 2012

(54) BRANCH VESSEL GRAFT METHOD AND DELIVERY SYSTEM (75) Inventors: Michael Wright, Allen, TX (US);
Samuel Arbefeuille, Hollywood, FL (US); Lalith Wijeratne, Cooper City, FL (US); Trevor Greenan, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1115 days.

(21) Appl. No.: 11/620,361

(22) Filed: Jan. 5, 2007

(65) Prior Publication Data
US 2008/0167704 A1    Jul. 10, 2008

(51) Int. Cl.
A61F 2/84 (2006.01)
A61F 2/06 (2006.01)

(52) U.S. Cl. ............... 623/1.35; 623/1.13; 623/1.16; 623/1.23

(58) Field of Classification Search ........ 623/1.13–1.16, 623/1.23, 1.35–1.36; 606/108, 194
See application file for complete search history.

(56) References Cited

U.S. PATENT DOCUMENTS

| | | | |
|---|---|---|---|
| 5,609,627 A | 3/1997 | Goicoechea et al. | |
| 5,632,772 A | 5/1997 | Alcime et al. | |
| 5,639,278 A | 6/1997 | Dereume et al. | |
| 5,669,924 A | 9/1997 | Shaknovich | |
| 5,676,697 A | 10/1997 | McDonald | |
| 5,683,450 A | 11/1997 | Goicoechea et al. | |
| 5,693,088 A | 12/1997 | Lazarus | |
| 5,697,970 A | 12/1997 | Schmitt et al. | |
| 5,723,004 A | 3/1998 | Dereume et al. | |
| 5,755,778 A | 5/1998 | Kleshinski | |
| 5,921,995 A | 7/1999 | Kleshinski | |
| 5,925,074 A | 7/1999 | Gingras et al. | |
| 5,961,548 A | 10/1999 | Shmulewitz | |
| 5,984,955 A * | 11/1999 | Wisselink | 623/1.35 |
| 6,030,414 A * | 2/2000 | Taheri | 623/1.1 |
| 6,033,434 A | 3/2000 | Borghi | |
| 6,039,754 A | 3/2000 | Caro | |
| 6,051,020 A | 4/2000 | Goicoechea et al. | |
| 6,059,824 A | 5/2000 | Taheri | |
| 6,074,416 A * | 6/2000 | Berg et al. | 623/1.36 |
| 6,086,611 A | 7/2000 | Duffy et al. | |
| 6,090,133 A | 7/2000 | Richter et al. | |
| 6,099,558 A | 8/2000 | White et al. | |
| 6,165,213 A | 12/2000 | Goicoechea et al. | |

(Continued)

OTHER PUBLICATIONS

Anderson, John L. et al., "Endoluminal Aortic Grafting With Renal and Superior Mesenteric Artery Incorporation by Graft Fenestration", J Endovasc Ther; 2001; 8:3-15.

*Primary Examiner* — Elizabeth Houston (57) ABSTRACT

A primary and branch graft deployment delivery system (70) comprises a primary graft (72) having a branch port opening or member (75), a retractable primary sheath containing the primary graft, an outer tube (60) within the retractable primary sheath and within the primary graft, an inner tube (61) within the outer tube, a cap (54 or 71) coupled to the inner tube and configured to retain at least a portion of a proximal area (73) of the primary graft in a radially compressed configuration. The system further comprises a branch graft (89) advanceable through the branch graft port member and further comprising a snap connector member (90) associated with the branch graft, the snap connector member being configured to frictionally engage the port member, the engagement of the snap connector to the port member forms a connection between the proximal end of the branch graft and the primary graft.

6 Claims, 10 Drawing Sheets

U.S. PATENT DOCUMENTS

| | | |
|---|---|---|
| 6,165,214 A | 12/2000 | Lazarus |
| 6,183,509 B1 | 2/2001 | Dibie |
| 6,187,033 B1 | 2/2001 | Schmitt et al. |
| 6,210,429 B1 | 4/2001 | Vardi et al. |
| 6,251,133 B1 | 6/2001 | Richter et al. |
| 6,254,593 B1 | 7/2001 | Wilson |
| 6,258,116 B1 | 7/2001 | Hojeibane |
| 6,264,682 B1 | 7/2001 | Wilson et al. |
| 6,287,335 B1 | 9/2001 | Drasler et al. |
| 6,293,955 B1 | 9/2001 | Houser et al. |
| 6,325,826 B1 | 12/2001 | Vardi et al. |
| 6,344,056 B1 | 2/2002 | Dehdashtian |
| 2001/0012959 A1 | 8/2001 | Blaeser et al. |
| 2001/0012962 A1 | 8/2001 | Schmitt et al. |
| 2001/0016768 A1 | 8/2001 | Wilson et al. |
| 2001/0037142 A1 | 11/2001 | Stelter et al. |
| 2002/0019659 A1 | 2/2002 | Goicoechea et al. |
| 2002/0035389 A1 | 3/2002 | Richter et al. |
| 2002/0156517 A1* | 10/2002 | Perouse .................. 623/1.11 |
| 2003/0093145 A1* | 5/2003 | Lawrence-Brown et al. .................. 623/1.21 |
| 2004/0059406 A1 | 3/2004 | Cully et al. |
| 2004/0093063 A1 | 5/2004 | Wright et al. |
| 2005/0273162 A1 | 12/2005 | Laguna |
| 2006/0155359 A1* | 7/2006 | Watson .................. 623/1.13 |
| 2006/0247757 A1 | 11/2006 | Kaufmann et al. |
| 2007/0179592 A1* | 8/2007 | Schaeffer .................. 623/1.35 |

* cited by examiner

BRANCH VESSEL GRAFT METHOD AND DELIVERY SYSTEM

FIELD OF THE INVENTION

This invention relates generally to medical devices and procedures, and more particularly to a method and system of deploying a branch vessel graft in a vascular system.

BACKGROUND OF THE INVENTION

Prostheses for implantation in blood vessels or other similar organs of the living body are, in general, well known in the medical art. For example, prosthetic vascular grafts formed of biocompatible materials (e.g., Dacron or expanded, porous polytetrafluoroethylene (PTFE) tubing) have been employed to replace or bypass damaged or occluded natural blood vessels. A graft material supported by framework is known as a stent-graft or endoluminal graft. In general, the use of stent-grafts for treatment or isolation of vascular aneurysms and vessel walls which have been thinned or thickened by disease (endoluminal repair or exclusion) are well known. Many stent-grafts, are "self-expanding", i.e., inserted into the vascular system in a compressed or contracted state, and permitted to expand upon removal of a restraint. Self-expanding stent-grafts typically employ a wire or tube configured (e.g. bent or cut) to provide an outward radial force and employ a suitable elastic material such as stainless steel or Nitinol (nickel-titanium). Nitinol may additionally employ shape memory properties. The self-expanding stent-graft is typically configured in a tubular shape of a slightly greater diameter than the diameter of the blood vessel in which the stent-graft is intended to be used. In general, rather than graft placement in a traumatic and invasive manner such as open surgery, stents and stent-grafts are preferably deployed through a less invasive intraluminal delivery, i.e., cutting through the skin to access a lumen or vasculature or percutaneously via successive dilatation, at a convenient (and less traumatic) entry point, and routing the stent-graft through the lumen to the site where the prosthesis is to be deployed.

Intraluminal deployment is typically effected using a delivery catheter with coaxial inner (plunger) and outer (sheath) tubes arranged for relative axial movement. The stent graft is compressed and disposed within the distal end of an outer catheter tube in front of an inner tube. The catheter is then maneuvered, typically routed though a lumen (e.g., vessel), until the end of the catheter (and the stent-graft) is positioned in the vicinity of the intended treatment site. The inner tube is then held stationary while the outer tube of the delivery catheter is withdrawn. The inner tube prevents the stent-graft from being withdrawn with the outer tube. As the outer tube is withdrawn, the stent-graft radially expands from a proximal end to a distal end of the stent-graft so that at least a portion of it is in substantially conforming surface contact with a portion of the interior of the lumen e.g., blood vessel wall or anatomical conduit. The proximal end of the stent-graft is the end nearest to the heart by way of blood flow whereas the distal end is the end furthest away from the heart during deployment.

Most stent-graft deployment systems are configured to have the proximal end of the stent-graft deploying as the outer tube or sheath is pulled back. The proximal end of the stent-graft is typically designed to fixate and seal in the vessel during deployment. Unfortunately, this configuration leaves little room for error in placement since re-positioning the stent-graft after initial deployment is usually not possible. Deploying the proximal end of the stent-graft first makes accurate pre-deployment positioning of the stent-graft critical.

One attempt to overcome this problem by W. L. Gore utilized a flexible jacket that deploys the stent-graft with a ripcord that opens the jacket along the longitudinal axis of the flexible jacket, e.g., U.S. Pat. No. 6,315,792. Unfortunately, this method introduced a separate non-integrated sheath into the system into the femoral artery and further failed to provide the desired control during deployment. Other stent-graft delivery systems have also attempted to confine the proximal end of the stent-graft, but generally fail to provide adequate control in manipulating the stent-graft positioning in both the initial deployment of the stent graft and the re-deployment of the stent-graft (once the stent-graft has been partially deployed). Another problem encountered with existing systems, particularly with systems that have a distal end of a stent-graft fixed during deployment (or during the uncovering of a sheath) is the frictional forces that can cause the stent-graft to axially compress or bunch up. This bunching increases the density of the stent-graft within the sheath and further increases the frictional drag experienced during deployment.

Another indication requiring further control in the deployment of stent-grafts is the need for an effective method of deploying branch grafts. Patients diagnosed with aneurysms involving renal arteries or other branch arteries are typically excluded from endovascular grafting because most endovascular grafting systems are not designed for use in regions of the aorta from which side branches extend. Most if not all of the endovascular grafts which have been designed for use in treating infrarenal aneurysms, for example, require that a proximal "neck" (e.g., at least two (2) centimeters of non-aneurysmic aorta) exist inferior to the renal arteries, to provide a region where the superior end of the graft may be securely anchored in place, without blocking or restricting blood flow into the renal arteries. The deployment of endovascular grafts within regions of the aorta from which branch arteries extend (e.g., regions of the aorta from which the renal, superior mesenteric, celiac, intercostal, and/or subclavian arteries emanate) present additional technical challenges because, in those cases, the endovascular graft must be designed, implanted and maintained in a manner which does not impair the flow of blood into the branch arteries.

U.S. Pat. No. 5,425,765 (Tiefenbrun et al.) describes an endovascular graft which has one or more openings or fenestrations formed at specific locations, to allow blood to flow from the aorta into one or more branch arteries. However, such fenestrations do not form discrete conduit(s) through which blood is channeled into each branch artery. As a result, the area surrounding the fenestrations could be prone to i) the leakage of blood into the space between the outer surface of the aortic graft and the surrounding aortic wall or ii) post-implantation migration or movement of the graft causing misalignment of the fenestration(s) and the branch artery(ies)—with resultant impairment of flow into the branch artery(ies).

U.S. Pat. No. 5,984,955 (Wisselink) describes a system and method for endoluminal grafting of a main anatomical conduit (e.g., the aorta) and various branch conduits (e.g., side branch vessels such as the carotid, innominate, subclavian, intercostal, superior mesenteric, celiac, or renal arteries-or furcations such as the iliac arteries) which emanate from the main anatomical conduit. The Wisselink grafting system generally comprises a primary graft having at least one opening therein for at least one branch graft which is passable through the opening of the primary graft and into the branch anatomical conduit(s) such that the proximal end of each branch graft is in substantially fluid-tight sealing contact with the primary graft. The embodiments discussed in Wisselink illustrate a protruding branch graft connector that protrudes from the main graft that includes a rigid or semi-rigid frustoconical member that extends outwardly. The protruding frustoconical member would likely add frictional forces during deployment of the main graft and would further impede efforts in any attempts to re-deploy the main graft in a different orientation or position once initially deployed and anchored. Additionally, the Wisselink system may experience difficulty tracking the branch graft through branch anatomical conduits without the use of a cap. The Wisselink system also discloses a main or primary graft that has first and second ends that fix or anchor to the main anatomical conduit during deployment of the branch grafts. In other words, the main graft in Wisselink is anchored before the complete deployment of both the main and branch grafts.

The accompanying figures include various showings of human anatomical structures, and such anatomical structures are labeled according to the following legend:

Aorta . . . A
Celiac Artery . . . CA
Femoral Artery . . . F
Heart . . . H
Iliac Arteries . . . IL (IL.sub.1 and IL.sub.2)
Kidneys . . . K
Renal Arteries . . . RA (RA.sub.1 and RA.sub.2)
Superior Mesenteric Artery . . . SMA As shown generally in FIGS. 1-1D, prior art endoluminal grafting system 10 generally comprises a primary graft 12 having at least one branch graft opening 14 formed therein, and at least one branch graft 16 which is advanceable out of the branch graft opening 14 and into a branch anatomical conduit (e.g., a side branch or furcation of a blood vessel). A branch graft connector apparatus 17 is incorporated into the primary graft 12 and/or branch graft(s) 16 to connect the proximal end of the branch graft(s) 16 to the primary graft 12. One or more primary graft anchoring devices 18, such as radially expandable stent(s) or frame(s), is/are used to frictionally hold the primary graft 12 in a fixed position in the lumen of the primary anatomical conduit (e.g., aorta). Also, where necessary, one or more branch graft anchoring devices 20, such as radially expandable stent(s) or frame(s), may be used to frictionally hold at least the distal end of the branch graft(s) 16 in fixed position in the lumen(s) of the branch anatomical conduit(s) (e.g., carotid, innominate, subclavian, intercostal, superior mesenteric, celiac, renal or iliac arteries). These primary graft anchoring device(s) 18 and branch graft anchoring device(s) 20 may be formed or incorporated into the body of the primary and branch grafts 12, 16 or, alternatively, they may be formed as separate structures (e.g., separate self-expanding or pressure-expandable stents) which are positioned within the lumens of the primary and branch grafts 12, 16, to accomplish the desired anchoring of the primary and branch grafts 12, 16, as shown.

Each branch graft opening 14 of the primary graft 12 is strategically placed, and preferably reinforced and marked for radiographic visualization, to facilitate precise alignment of each branch graft opening 14 with the particular branch anatomical conduit (e.g., carotid, innominate, subclavian, intercostal, superior mesenteric, celiac, renal or iliac arteries) into which its branch graft 16 is to extend. The desired strategic placement of each branch graft opening 14 may be facilitated by custom-forming the branch graft opening(s) 14 in the primary graft 12, prior to implantation of the primary graft 12. Such pre-implantation, custom formation of the branch graft opening(s) 14 may be accomplished through the use of spiral computed tomography data of the vascular anatomy of the particular patient in whom the endovascular grafting system 10 is to be implanted. Notably, in applications where the primary graft 12 is being prepared for implantation in the thoracic or thoracoabdominal aorta, the branch graft openings 14 may be sized and positioned to align with relatively small side branch vessels (e.g., carotid, innominate, subclavian, intercostal, superior mesenteric, celiac, or renal arteries) which, unlike the iliac bifurcation at the inferior end of the aorta, require a branch graft 16 be passable through such branch graft opening(s) 14 and into the smaller side branch vessel (e.g., carotid, innominate, subclavian, intercostal, superior mesenteric, celiac, or renal arteries) at an angle of approximately 80-90 degrees upwardly or downwardly relative to the axis of the aorta.

Once mapped a customized stent graft with branch graft opening(s) 14 having been formed at the mapped side branch locations (including branch graft connector(s) 17), the primary graft 12 is inserted via an introducer into the femoral artery, and advanced under radiographic guidance into the site (e.g., the aneurysm) where the primary graft 12 is to be deployed. This insertion of the primary graft 12 (and any primary graft anchoring device(s) 18 which are formed separately from the graft 12) may be facilitated by mounting the primary graft 12 (and any such separate graft anchoring devices 18) on a balloon catheter or other suitable delivery catheter capable of carrying the primary graft (and any separate graft anchoring device(s) 18) to the intended site of deployment. The primary graft 12 and any separate primary graft anchoring device 18 is/are then radially expanded or otherwise deployed such that the primary graft becomes anchored in a substantially fixed position within the primary anatomical conduit (e.g., aorta A). In applications wherein the endoluminal grafting system 10 is being used to repair an aneurysm, the hemodynamic pressure within the aneurysm sac (i.e., the space within the aneurysm but outside the primary graft 12), as well as the hemodynamic pressure within the branch anatomical conduit(s) which emanate from the aneurysm, will be substantially unaffected by the initial placement of the primary graft 12 because, until such time as the branch graft(s) 14 have been introduced, blood will continue to flow out of the branch graft opening(s) 14 of the primary graft 12.

After the primary graft 12 has been positioned and anchored within the primary anatomical conduit (e.g., aorta A), a guidewire 30 may be transluminally advanced through the lumen of the primary graft 12, out of a branch opening 14 and into the branch anatomical conduit (e.g., In some applications, a guide catheter may be introduced into the lumen of the primary graft 12 to facilitate passage of the guidewire 30 out of the desired branch graft opening 14.

A branch graft 16 is then mounted on a balloon catheter 32, and the distal end of the branch graft may be drawn taught about the catheter balloon 34 by a purse string suture 36 (e.g., 7.0 polypropylene suture material). The balloon catheter 32 having the branch graft 16 mounted thereon is then advanced over the guidewire 30 until the proximal end of the branch graft 16 becomes connected to the branch graft opening 14 of the primary graft 12 by way of the branch graft connector apparatus 17. Thereafter, the catheter balloon 34 is inflated, causing the purse string suture 36 to break and the distal end of the branch graft 16 to radially expand into contact with the surrounding wall of the branch anatomical conduit.

Figure 1:
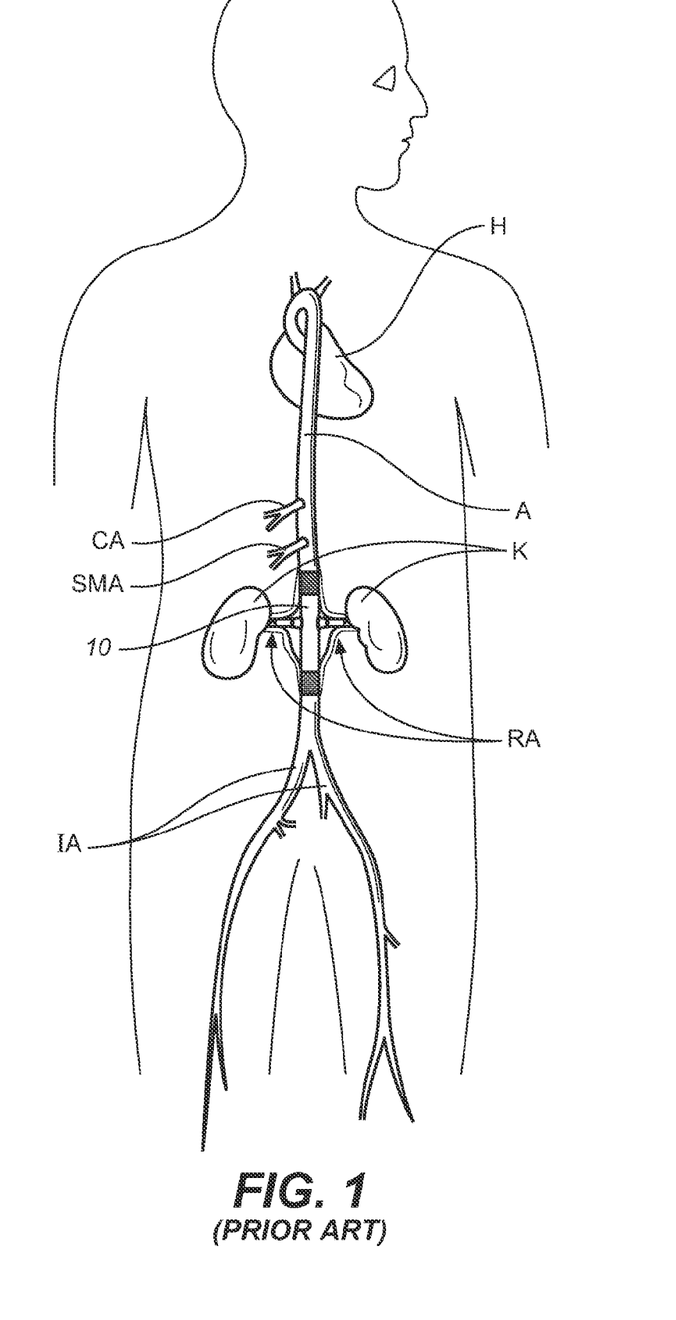
FIG. 1 is a schematic showing of a human body having a prior art endoluminal grafting system implanted to repair an abdominal aortic aneurism which involves the renal arteries.
Figure 1A:
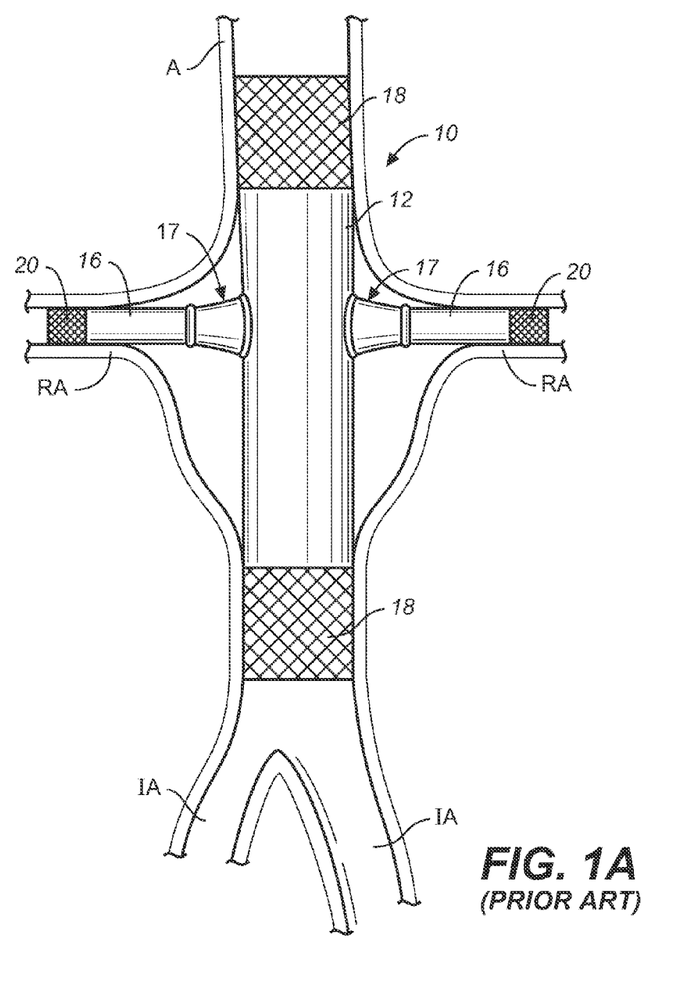
FIG. 1A is an enlarged view of the perirenal aorta and endovascular grafting system shown in FIG. 1.
Figure 1B:
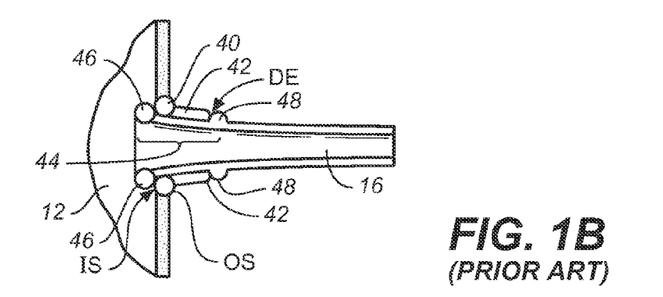
FIG. 1B is a partial cross sectional view of an endoluminal grafting system of FIG. 1, showing connectors for connecting the proximal end of the branch graft to the primary graft.
Figure 1C:
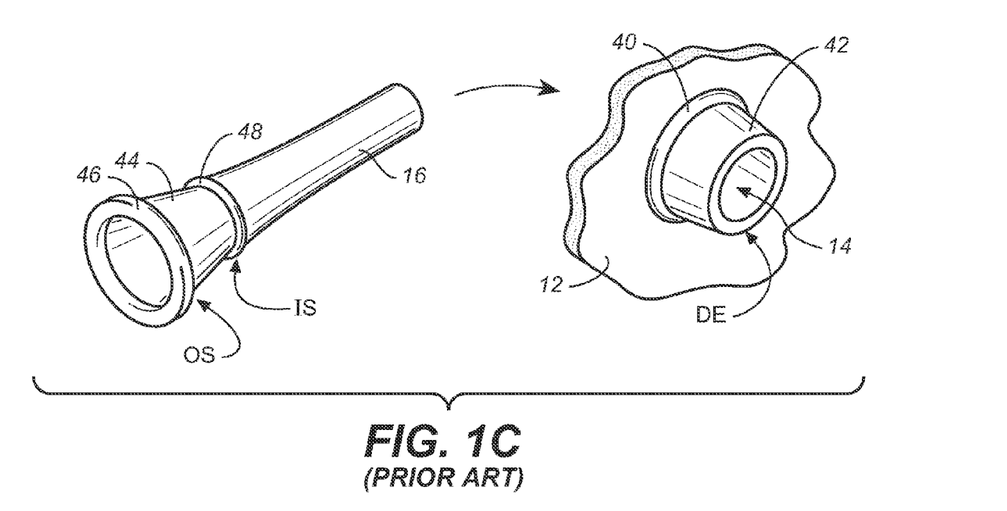
FIG. 1C is an exploded perspective view of the graft components shown in FIG. 1B.
Figure 1D:
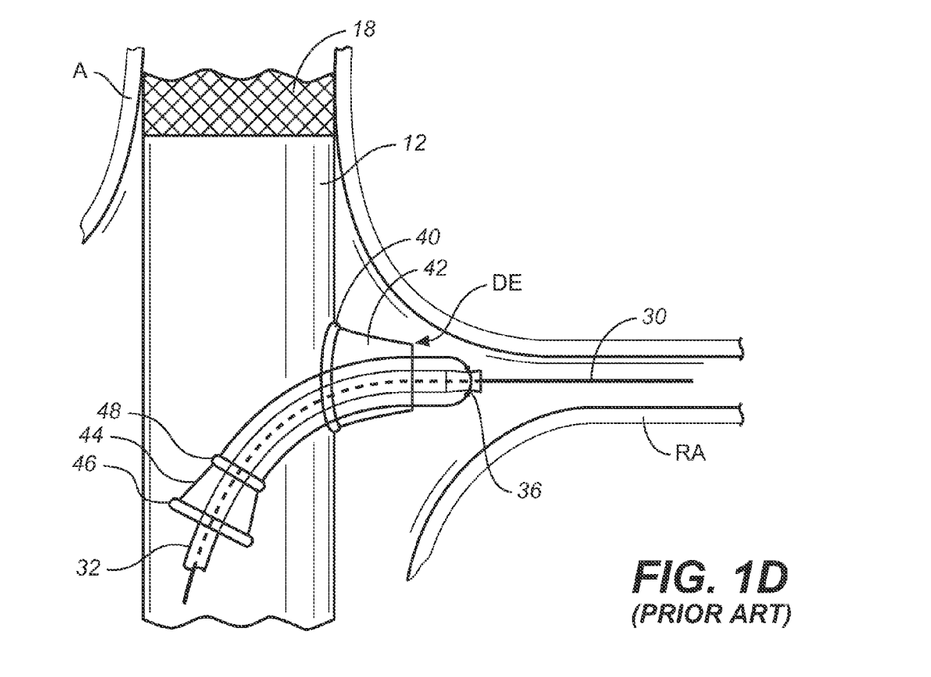
FIG. 1D shows the branch graft insertion step in the method for placing the branch graft(s) of the endoluminal grafting system of FIGS. 1A-1C after the primary graft has been implanted.
Figure 2A:
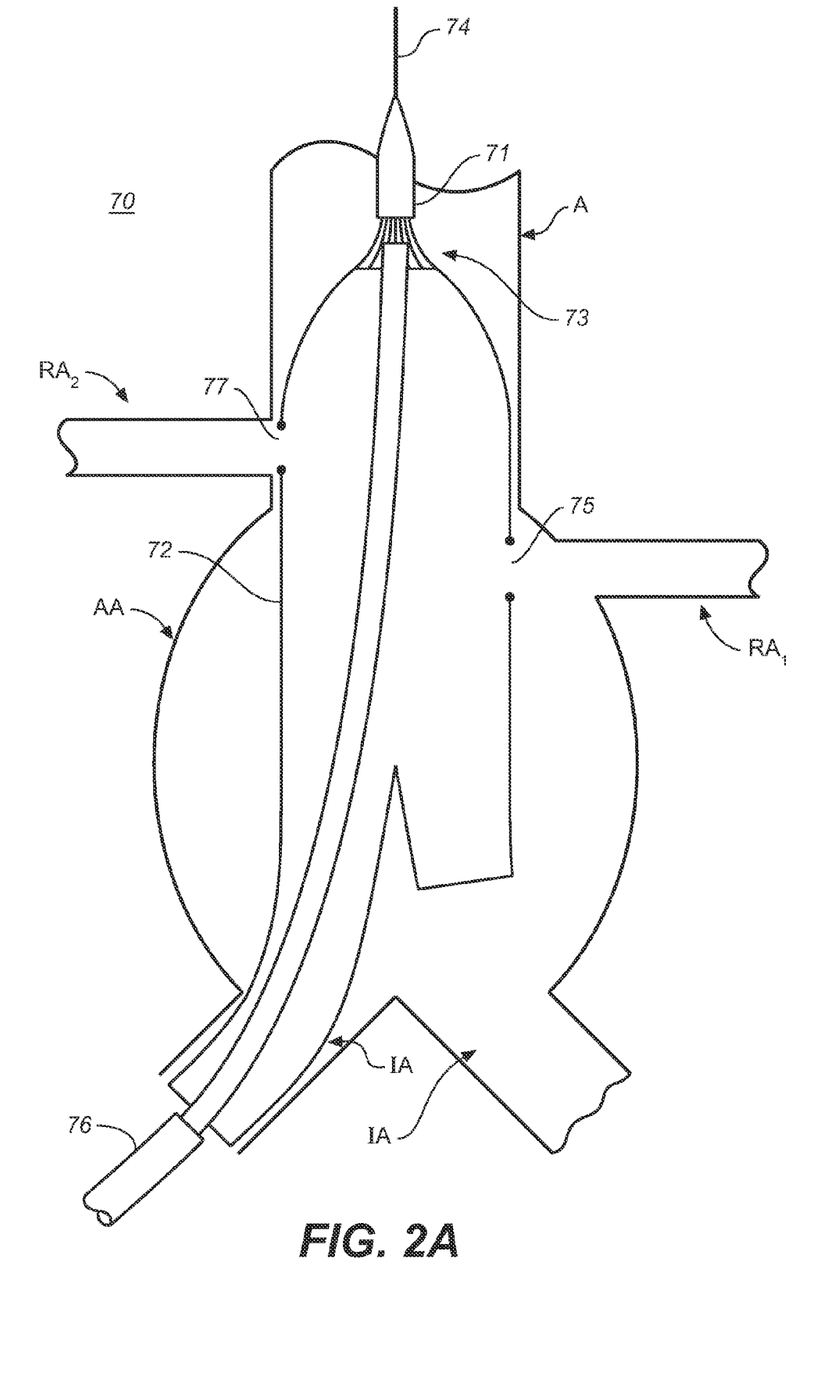
FIG. 2A is a schematic showing of a portion of a human aorta having a main body endoluminal stent graft with side branch openings with the proximal end of the stent graft still constrained by its delivery system.
Figure 2B:
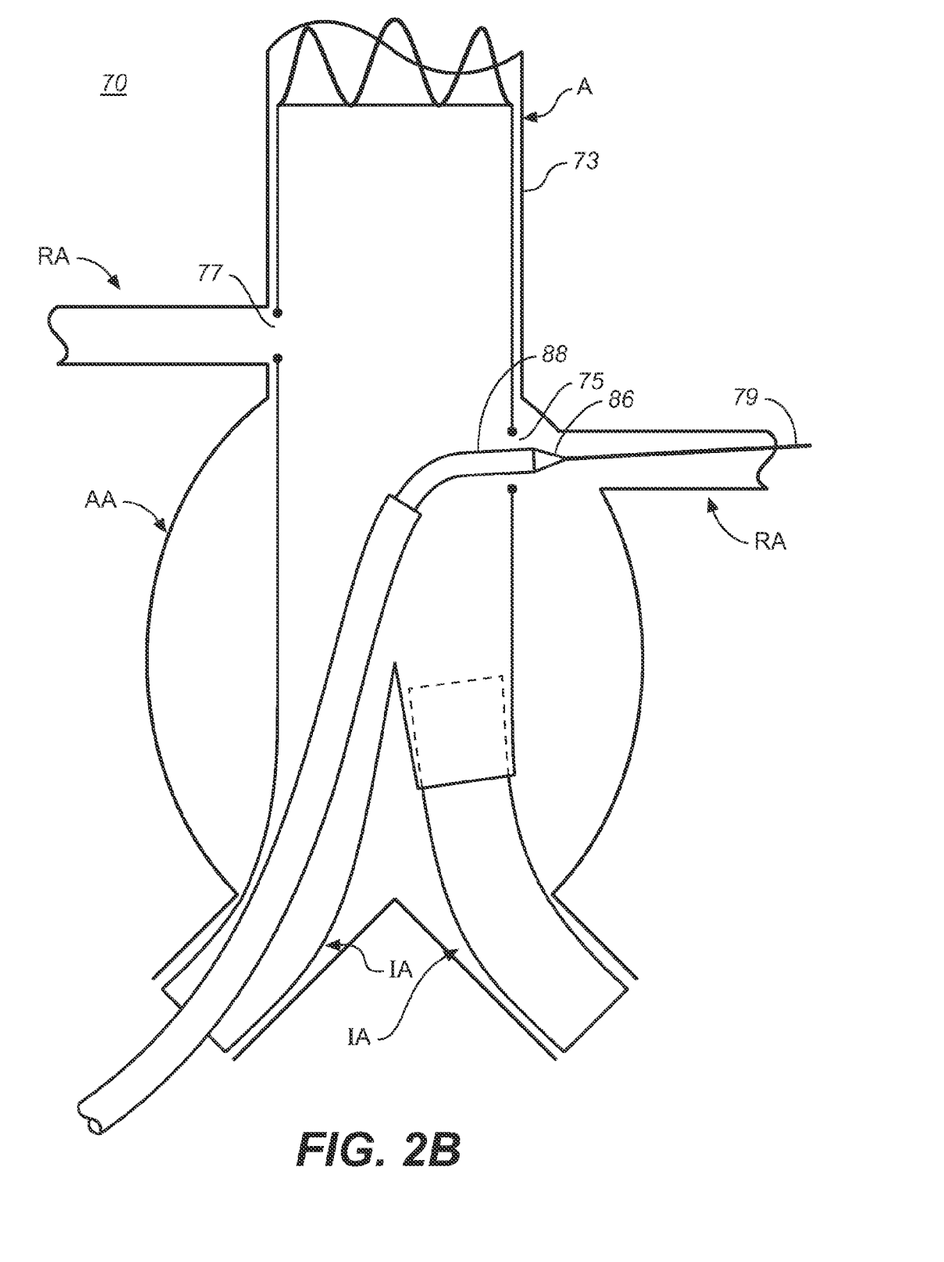
FIG. 2B is another schematic showing tracking and deployment of a branch graft through the main body stent graft in accordance with the present invention.
Figure 2C:
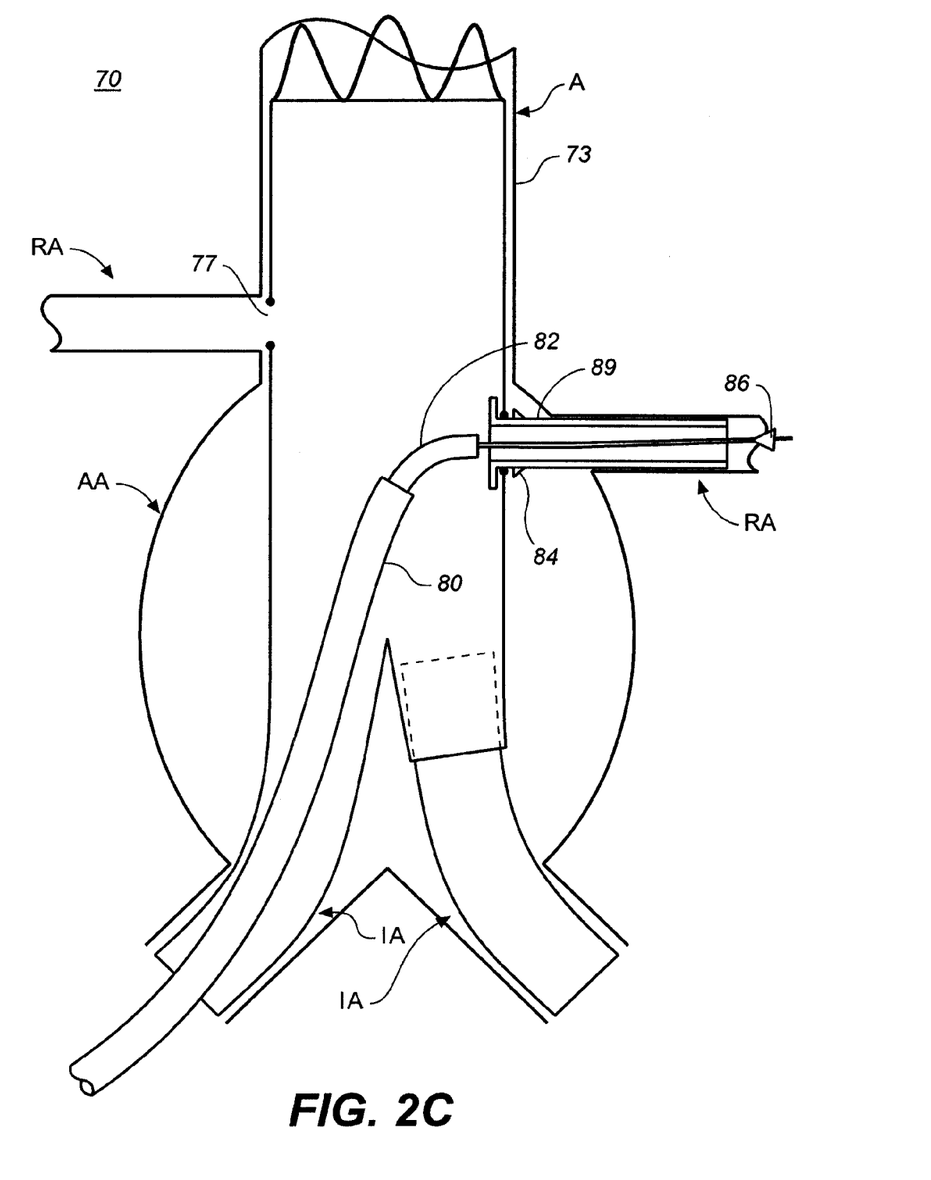
FIG. 2C is a schematic showing the branch graft positioned in the branch vessel by the branch delivery catheter.
Figure 2D:
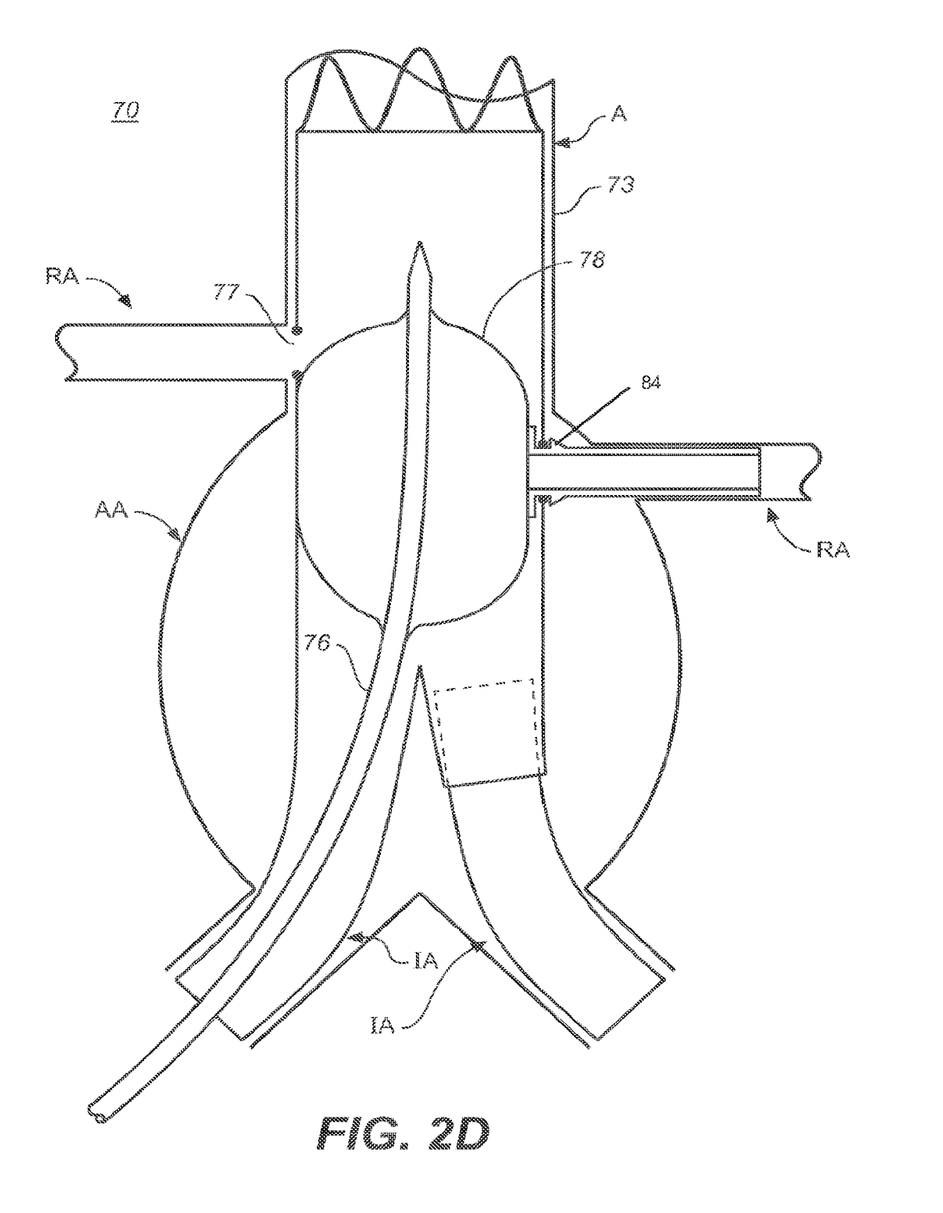
FIG. 2D is a schematic showing the final step of deployment of the branch graft: urging into engagement, a snap connection between the branch graft and the primary graft using a balloon catheter in accordance with the present invention.

A branch graft connector apparatus 17 is shown in detail in FIGS. 1B-1D. The components of this branch graft connector apparatus 17 associated with the primary graft 12 comprise: a first rigid or semirigid ring 40 which surrounds the branch graft opening 14, and a rigid or semirigid frustoconical member 42 which extends outwardly from the first ring member 40, as shown in FIG. 1B. The components of this branch graft connector apparatus associated with the branch graft 16 comprise a rigid or semirigid, tapered proximal portion 44, a second rigid or semirigid ring member 46 on the proximal end of the tapered proximal portion 44, and a third rigid or semirigid ring member 48 formed about the tapered proximal portion 44 at a spaced distance from the second ring member. The distance between the outer surface OS of the second ring member 46 and the inner surface IS of the third ring member 48 is substantially the same as the distance between the inner surface IS of the first ring member 40 and the distal end DE of the frustoconical member 42. In this manner, as the branch graft 12 is advanced, distal end first, out of the branch graft opening 14 it will reach a point of maximum advancement where at the inner surface IS of the first ring member 40 will abut against the outer surface OS of the second ring member 46, and the distal end DE of the frustoconical member 42 will abut against the inner surface IS of the third ring member 48. This will create a substantially fluid-tight seal between the proximal end of the branch graft 16 and the body of the primary graft 12. Additionally, this may form a snap-fit connection which will prevent the branch graft 14 from slipping or undergoing inadvertent retraction back into the lumen of the primary graft 12.

It will be appreciated that an audible or tactilely discernible indicator (e.g., a "snap") may occur as the separate components of the branch graft connector 17 come together, thereby indicating to the operator that the desired engagement and sealing of the proximal end of the branch graft 16 to the primary graft 12 has been accomplished.

Thus, a need exists for a method and deployment system that enables partial deployment of a stent-graft while constraining a proximal end of the stent-graft, provides adequate control to enable re-deployment of the stent-graft in various dimensions and further reduces deployment forces during advancement of the stent-graft to enable aligned deployment of branch grafts with corresponding branch vessel openings. Ideally, such a branch graft is a part of a system of grafts that can treat no-neck and thoraco-abdominal aortic aneurysms using a branch that makes a fluid tight connection to a port of the main graft.

In addition, there remains a need in the art for the development of new endovascular grafting systems and methods which a) may be useable for endovascular grafting in regions of a blood vessel (e.g., aorta) from which branch blood vessels (e.g., carotid, innominate, subclavian, intercostal, superior mesenteric, celiac, renal or iliac arteries) extend, and/or b) may enable more aortic aneurysm patients to be considered as candidates for endovascular repair, and/or c) may otherwise advance the state of the art of endovascular grafting to improve patient outcomes or lessen complications.

SUMMARY OF THE INVENTION

A main stent-graft and branch graft deployment delivery system includes a main stent-graft having a branch graft opening, a retractable primary sheath containing the main stent-graft in a first constrained diameter configuration, an outer tube within the retractable primary sheath and within the main stent-graft, and an inner tube within the outer tube, where the inner tube and the outer tube both axially move relative to the retractable primary sheath and to each other. The system further includes a cap coupled to a distal end of the inner tube and configured to retain at least a portion of a proximal area of the stent-graft in a radially compressed configuration.

In another aspect according to the present invention, a main stent-graft and branch graft deployment delivery system comprises a main stent-graft having a branch graft opening including a port member, a retractable primary sheath containing the main stent-graft in a first constrained diameter configuration, an outer tube within the retractable primary sheath and within the main stent-graft, an inner tube within the outer tube, wherein the inner tube and the outer tube both axially move relative to the retractable primary sheath and to each other, and a cap coupled to a distal end of the inner tube and configured to retain at least a portion of a proximal area of the main stent-graft in a radially compressed configuration. The system further comprises a tubular branch graft having a lumen extending longitudinally therethrough and being advanceable through the branch graft port member and further comprising a snap connector member being associated with the proximal end of the branch graft, the snap connector member being configured to frictionally engage the port member as the proximal end of the branch graft is brought into approximation with the branch graft opening of the primary graft, the engagement of the snap connector to the port member being operative to form a connection between the proximal end of the branch graft and the primary graft.

In another aspect according to the present invention, a main stent-graft and branch graft deployment delivery system comprises a retractable primary sheath, an outer tube within the retractable primary sheath, an inner tube within the outer tube, wherein the inner tube can move axially relative to the outer tube, a cap coupled to a distal end of the inner tube, and a retention mechanism attached to the outer tube for retaining a proximal area of a main stent-graft in a constrained diameter configuration while remaining within the cap while still enabling axial and radial movement of the stent-graft. The system further comprises a tubular branch graft having a lumen extending longitudinally therethrough, the branch graft being advanceable through a branch graft port member in a branch opening in the main stent-graft and further comprising a snap connector member being associated with the proximal end of the branch graft, said snap connector member being configured to frictionally engage the port member as the proximal end of the branch graft is brought into approximation with the branch opening of the main-stent graft, the engagement of the snap connector to the port member being operative to form a connection between the proximal end of the branch graft and the main stent-graft graft.

In another aspect according to the present invention, a method of deploying a branch graft through at least a partially deployed primary graft having a branch port opening, comprises the steps of constraining a proximal end of the primary graft while feeding the branch graft in a constrained configuration through a lumen of the primary graft and substantially through the branch port opening and inflating a balloon in the primary graft causing a snap connector on the branch graft to connect with the branch port opening.

In another aspect according to the present invention, a method for deployment of a main stent-graft and a branch graft comprises the steps of constraining a proximal area of a stent-graft radially under a cap while at least partially deploying a remaining portion of the main stent-graft, adjusting at least one of the axial and radial positions of the main stent-graft after the partial deployment the remaining portion, and releasing the proximal area of the main stent-graft by minimal controlled coaxial movement between the cap and a tube retaining the main stent-graft within the cap.

In yet another aspect according to the present invention, a method for deployment of a main stent-graft and a branch graft comprises the steps of constraining a proximal area of the main stent-graft radially under a cap while partially deploying a remaining portion of the main stent-graft, wherein the main stent-graft further includes at least one substantially flush branch vessel port, adjusting at least one of the axial and radial positions of the stent-graft after the partial deployment the remaining portion to align the substantially flush branch vessel port with a branch vessel, and releasing the proximal area of the stent-graft by minimal controlled coaxial movement between the cap and a tube retaining the stent-graft within the cap.

DETAILED DESCRIPTION

The various drawings illustrate several embodiments and aspects of branch graft deployment systems according to the present invention.

The prior art system described in the background has many common elements of the general structure and function of endoluminal grafting systems for branched anatominal conduits according to the present invention. Several distinctions will illustrate the novel improvements therein.

The primary graft or main stent-graft and branch graft deployment system 70 of FIGS. 2A-D is similar to the system 10 of FIGS. 1-1D except for various key features that would enable greater control, trackability, and maneuverability for both the primary and branch grafts even after partial deployment of the primary graft 72. As in system 10, the system 70 can include a deployed bifurcated primary graft 72 having a port or branch graft opening 75 or additional ports 77 as needed, a catheter system 76 including a retractable primary sheath, an outer tube within the retractable primary sheath, an inner tube within the outer tube wherein the inner tube can move axially relative to the outer tube along a track formed by a guidewire 74 or guidewires, and a cap 71 coupled to a distal end of the inner tube, a retention mechanism attached to the outer tube for retaining a proximal area 73 of the main stent-graft in a constrained diameter configuration while remaining within the cap while in a pre-completely deployed configuration still enabling axial and radial movement of the main stent-graft. The retention mechanism, inner and outer tubes, and cap at the distal end of the inner tube will be explained and seen in greater detail in conjunction with the description of FIGS. 3A-B.

After the primary graft (bifurcated body) 72 has been positioned and anchored within the primary anatomical conduit (e.g., aorta A) and a contralateral leg 72a has been delivered and deployed in the open port (or a short leg) of the main body 72, branch guidewire 79 with or without the aid of a guide catheter can be transluminally advanced through the primary graft 72, out of a branch opening 75 and into the branch anatomical conduit RA1. Similarly a guide catheter and guidewire can be routed through the primary graft 72 to pass the guidewire out of other desired branch graft opening 77 and into its the respective branch anatomical conduit, e.g. RA2.

A branch graft 89 mounted on a balloon catheter 80, is configured so that the distal end of the branch graft can be constrained about the catheter balloon (not shown) using a constraint sleeve 88 and conical cap 86 instead of a purse string suture as shown in FIG. 1D. The balloon catheter with the branch graft 89 mounted thereon is then advanced over the guidewire preferably using a pushrod 82 as a compressive force transmitting member until the proximal end of the branch graft 89 becomes connected (engaged) to the branch graft opening 75 of the primary graft 72 by way of the branch graft connector 84. Thereafter, the branch catheter balloon within the constraint sleeve 88 is inflated, causing the cap 86 to invert and the constraint sleeve 88 to break and the distal end of the branch graft 89 to radially expand into contact with the surrounding wall of the branch anatomical conduit. Inflating balloon 78 of the balloon catheter 76 in the primary graft will provide the required outward force to further engage (or more fully engage) the branch graft connector 84 with the branch graft opening 75 or port to preferably form a substantially fluid-tight seal between the proximal end of the branch graft 89 and the body of the primary graft 72. Note that the conical cap 86 preferably provides a smooth taper tip for tracking into the branch artery and the constraint sleeve 88 preferably comprises a seam that opens when the balloon is inflated. This breakaway sleeve (88) keeps the branch graft's profile low and surface smooth for improved trackability before deployment.

Ideally, the deployment system 70 comprises a tapered tips (71 and 86) that are flexible and able to provide trackability in tight and tortuous vessels. The tapered tip can include a lumen allowing for passage of a guidewire for example. Other tip shapes such as bullet-shaped tips could also be used.

Figure 3A:
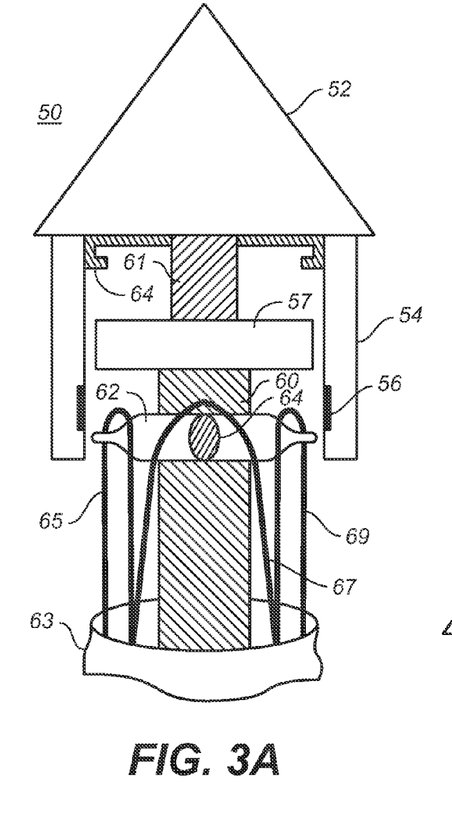
FIG. 3A is a close up schematic view of the stent-graft deployment delivery system with a plurality of proximal springs constrained within a cap, e.g., as pictured in FIG. 2A.
Figure 3B:
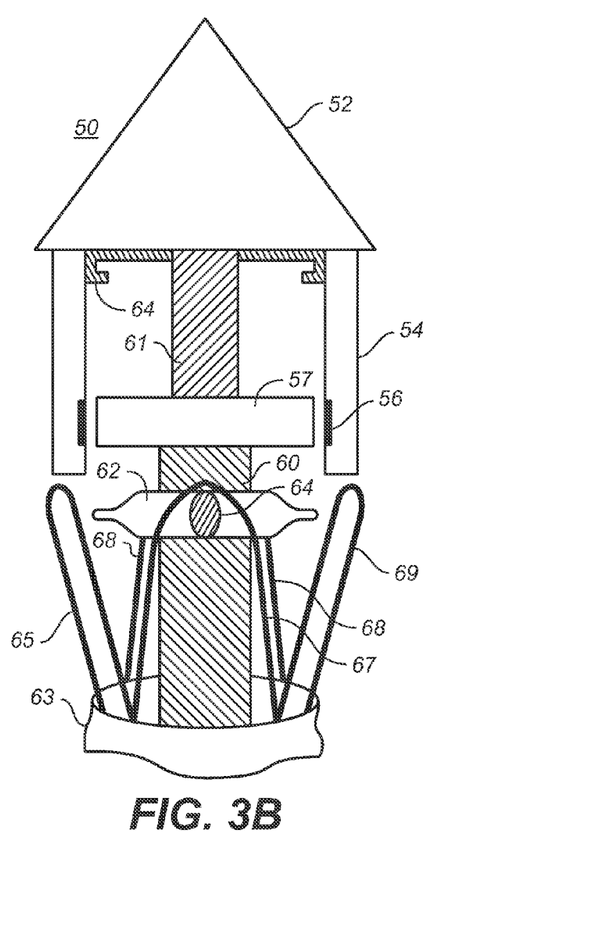
FIG. 3B illustrates the deployment delivery system of FIG. 3A with the plurality of proximal springs released from under the cap.

The retractable primary sheath (preferably made of a semi-rigid material such as polyethylene) in an un-retracted position contains the stent-graft 72 in a first constrained diameter configuration before initial deployment. Close up schematic plan views of another stent-graft deployment delivery system 50 are shown in FIGS. 3A and 3B. FIG. 3A illustrates a plurality of proximal springs 65, 67 and 69 (68 is hidden in this view) of a stent-graft 63 constrained within a cap (54) or shroud portion of a tip 52. The cap or shroud portion can be formed from the tube section 54 which can further include support ring 56. FIG. 3B illustrates another close up view of the stent-graft deployment delivery system 50 with the plurality of proximal springs 65, 67, 69 and 68 released from under the cap. The system 50 can include an outer tube 60 within the retractable primary sheath (not shown) and within the stent-graft 63. The system 50 can further include an inner tube 61 within the outer tube 60 serving as a guidewire lumen. The inner tube 61 and the outer tube 60 preferably move axially relative to each other and can also move relative to the retractable primary sheath. The system 50 further comprises a cap 54 coupled to a distal area or end of the inner tube 61 and further configured to retain at least a portion of a proximal area of the stent-graft 63 in a radially compressed configuration. A controlled relative axial movement between the outer tube 60 and the inner tube 61 releases the proximal end of the stent-graft (such as proximal springs) from the cap and from the radially compressed configuration.

The cap 54 can be formed from a shroud portion of the tapered tip 52 which is coupled at the distal end of the inner tube 61. Within the shroud portion (formed by the tubular body portion of the cap 54) preferably resides a back plate 57 coupled to a distal area or end of the outer tube 60 that serves as a proximal stop for the stent-graft 63. The tubular body portion of the shroud portion may also include a support ring 56 near the proximal end of the tapered tip 52 to provide additional rigidity to the cap 54. Additionally, a proximal lock 62 is also coupled to a distal area of the outer tube 60. The proximal lock 62 preferably includes at least one or a plurality of ribs 64 that serves as an axial constraint for the stent-graft 63. The proximal end (or the proximal springs 65, 67, 68 and 69) of the stent-graft 63 cannot deploy until the proximal lock clears the shroud portion of the tip.

A stent-graft can include a polyester or Dacron material (forming the graft material) sewn to a Nitinol support structure using polyester sutures. The Nitinol wire is used to form a skeletal structure that provides support, strength and stability to the stent-graft. The stent-graft can also have a support member on the proximal end of the stent-graft that if left mainly uncovered by the graft material. The uncovered portion will typically have a sinusoidal pattern with a predetermined number of apexes protruding up. The apexes form what is known as the proximal spring or springs of the stent-graft. As shown, the gap between the back plate 57 and the proximal lock 62 is preferably designed to hold the protruding apexes of the proximal spring. The apexes straddle the ribs 64 of the proximal lock 62 and remain trapped between the back plate 57 and the proximal lock until the relative movement between the outer tube 60 and the inner tube 61 exposes the gap and the proximal springs 65, 67, 68, and 69. In other words, the apexes cannot release from the ribs 64 on the proximal lock 62 while the apexes remain within the shroud portion of the cap 54. When the inner tube 61 and coupled tapered tip 52 are advanced forward exposing the proximal lock 62, the apexes of the proximal springs 65, 67, 68, 69 release from the respective ribs 64 of the proximal lock 62. The release results in the deployment of the proximal end of the stent-graft 63. Note that while the proximal springs 65, 67, 68, 69 remain in the gap and within the cap or shroud portion of the tapered tip 52, the proximal springs remain axially constrained as well as radially constrained. The support ring 56, usually made of metal, helps prevent the radial force of the proximal springs from distorting the shape of the tapered tip and particularly the shroud portion of the tapered tip.

Figure 4A:
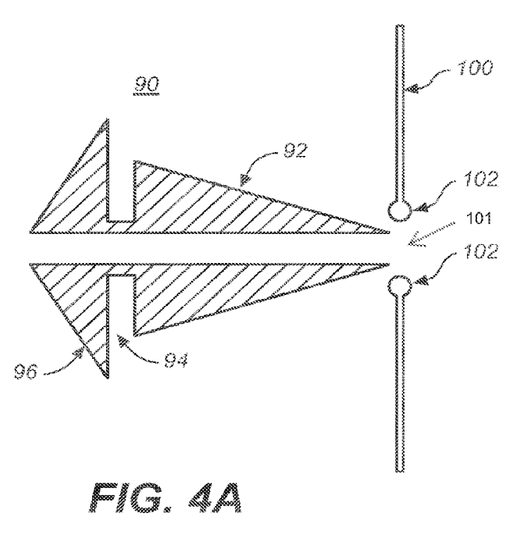
FIG. 4A is a schematic illustrating the snap connector before engagement with the port member in accordance with the present invention.
Figure 4B:
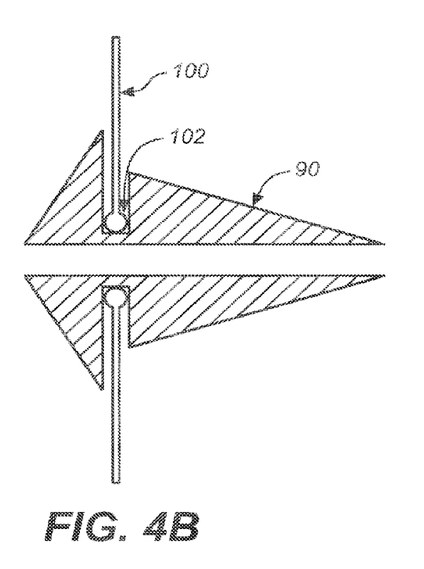
FIG. 4B is a schematic illustrating the snap connector of FIG. 4A engaged with the port member of the primary graft in accordance with the present invention.
Figure 5:
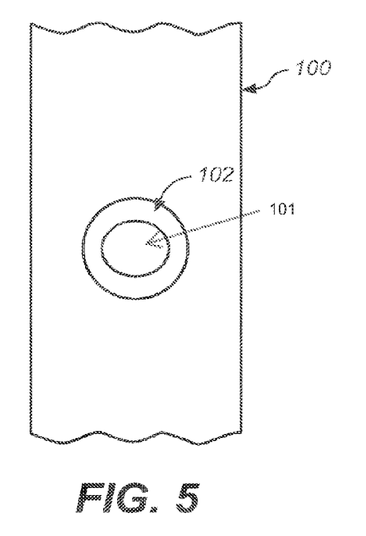
FIG. 5 is a side view of the primary graft illustrating the port member in accordance with the present invention.
Figure 6A:
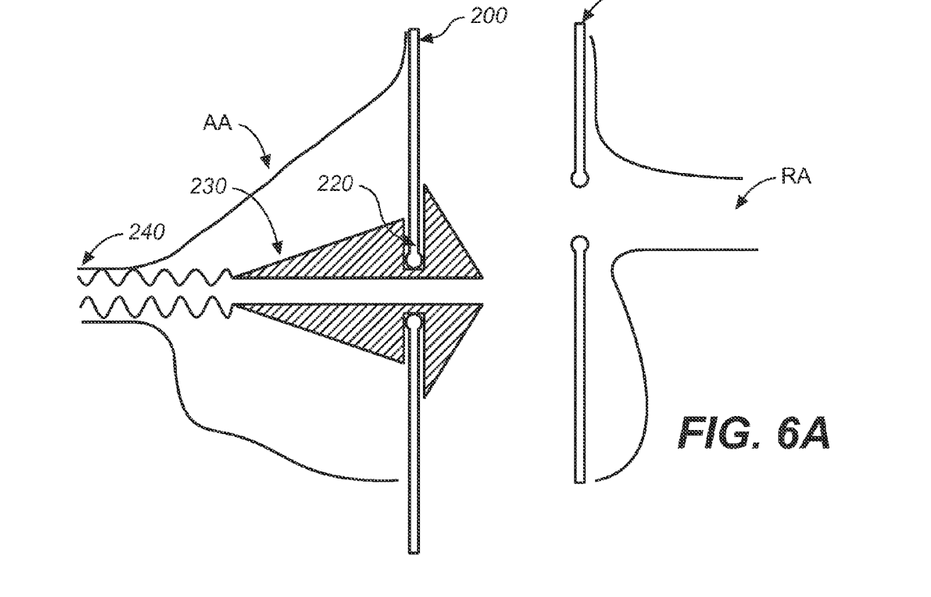
FIG. 6A is a schematic showing a branch graft connected to a primary graft while bridging a gap within the aneurysm to reach the branch artery in accordance with the invention.

Referring to FIGS. 4A, 4B and 5, an exemplary port member connector 90 is illustrated that can be used to engage with a branch graft opening or port 101 of a primary graft 100 in accordance with the present invention. Connector 90 is preferably a snap fit connector that can be integrated with the branch graft (as shown in FIGS. 6A & B). Preferably, the connector 90 is arranged and constructed with a flexible polymer and geometry that would allow the branch graft to traverse into the branch graft port 101 of the primary graft 100 and allow the port to be caught by a channel 94 of the connector. The connector 90 preferably includes a tapered leading edge 92 that aids in the transition of the port 101 on the primary graft 100 into the connection channel 94. The tapered leading edge 92 will compress and/or the port 101 will expand during engagement. Once past the tapered leading edge 92, the port 101 seats in the connection channel 94. The connector 90 further preferably includes a flange 96 that conforms to the interior of the primary graft 100 and ideally prevents the branch graft from migrating into the branch artery or conduit. The profile of the entire snap connection cannot be so great that it would require unreasonably large sized lumens to introduce it to the connection site. The channel 94 and port member 102 can also be formed of radiographically visible material to enable the operator to radiographically confirm that the branch graft has been firmly connected to and engaged with the primary graft. Additionally, it is to be appreciated that the branch graft connector 90 need not necessarily be a mechanical connector apparatus as shown in the drawings, but may alternatively comprise any mechanical, electromagnetic, frictional, or chemical (e.g., adhesive, coupling, or fusing agent) capable of joining the proximal end of the branch graft to the primary graft 100 in substantially fluid-tight sealing contact.

Figure 6B:
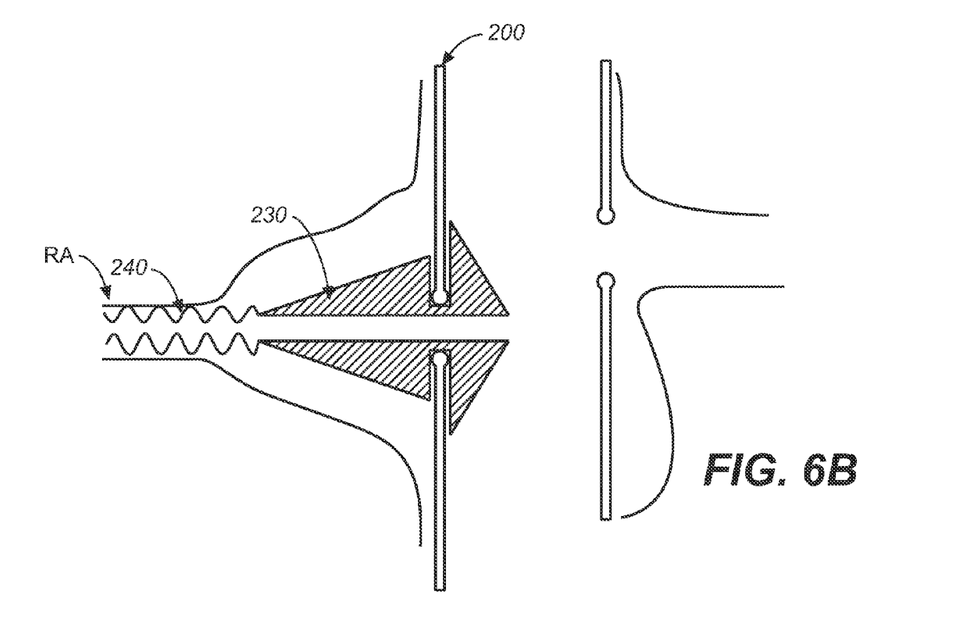
FIG. 6B is another schematic showing the branch graft of FIG. 6A after the aneurysm remodels.

Referring to FIG. 6A, a schematic is shown illustrating a branch graft 240 connected to a primary graft 200 while bridging a gap within the aneurysm (AA) to reach the branch artery (RA) in accordance with the invention. The branch graft is preferably integrated with a port member connector 230 including a channel 220 therein. The port member connector can be a silicone snap connector having other materials such as barium sulfate powder mixed with the silicone. When formed, the silicone mixed with barium sulfate imbeds into the graft material during the molding process. FIG. 6B is another schematic showing the branch graft of FIG. 6A after the aneurysm remodels. The body of the branch graft 240 preferably comprises of a tubular medical grade graft material such as Dacron or polyester or ePTFE. Sheets of this material can be cut and seamed to the appropriate diameter and length tubular shape for a given patient. The branch graft can be manufactured with crimps that help the branch graft resist kinking and allow it to stretch and contract. The crimp ideally forms a threaded cylindrical pattern that allows the branch graft to take on a characteristic of a spring. The ability to stretch and contract while resisting kinking will aid the graft when faced with gaps between the port of the main graft and the branch vessel (as shown in FIGS. 6A & B). These gaps occur because the aneurysm can incorporate the area of the branch vessel. The system must also maintain integrity and exclusion of the aneurysm during remodeling. Remodeling of the aneurysm can occur when the aneurysm has been excluded and changes size and shape.

When treating Abdominal Aortic Aneurisms (AAA), for example, there are several anatomical challenges when advancing a stent-graft deployment system or device and appropriately placing the stent-graft itself. A major challenge is encountered in the region of the aortic bifurcation (this typically includes the femoral, external iliac, and common iliac arteries). Existing main stent-graft delivery systems that deploy from a distal end of the stent-graft fail to provide sufficient options for re-alignment once the stent-graft is even partially deployed. Existing stent-graft delivery systems that deploy from a proximal end of the stent-graft fail to provide adequate control in the eventual release of the proximal end of the stent-graft. Stent-grafts that require alignment of ports with branch arteries can use the re-deployment capabilities and the controlled release mechanisms according to the present invention to a great advantage. Since the system constrains the proximal end of the stent-graft radially while allowing a portion of the middle of the stent-graft to deploy first, the stent-graft can be repositioned both axially, rotationally, and radially by preventing the stent-graft from fixating itself completely to a vessel, even when partially deployed.

Stent-grafts that require alignment with branch arteries can have the middle or port areas of the stent-graft release first. The stent-graft can be realigned so that all ports are properly aligned before releasing the proximal end of the stent-graft. The proximal end of the stent-graft is also axially constrained which enables the delivery system to maintain the position of the stent-graft during the full deployment sequence event if the stent-graft has little or no axial support. Since the present invention fixes the proximal end of the stent-graft during deployment while the sheath is withdrawn, the frictional forces between the stent-graft and sheath cause the stent-graft to be held under a tensile load. While under a tensile load, the density of the stent-graft and the compressive forces within the sheath are reduced. Additionally, using this design, deployment forces can be further reduced by removing supports (such as connecting bars) in the stent-graft since such supports would no longer be needed for deployment.

Additionally, the description above is intended by way of example only and is not intended to limit the spirit and scope of the invention and it equivalent as understood by persons skilled in the art.

What is claimed is:

1. A system for endoluminal grafting of an anatomical conduit having at least one branch anatomical conduit emanating therefrom, said system comprising:

a tubular primary graft configured for deployment in the anatomical conduit, said primary graft having proximal and distal ends and a lumen extending longitudinally therethrough, and a branch graft opening formed at a first location in the primary graft, the branch graft opening including a port member disposed around the branch graft opening, a distal end of the port member being substantially flush with an outer surface of the primary graft, the primary graft configured to be disposed in a substantially fixed position within the lumen of the anatomical conduit such that the branch graft opening is substantially aligned with the branch anatomical conduit; and, a tubular branch graft configured for deployment into the branch anatomical conduit, said branch graft having a proximal end, a distal end, and a lumen extending longitudinally therethrough, and said branch graft being advanceable through the branch graft opening and into the branch anatomical conduit, the branch graft including a snap connector member configured to frictionally engage the port member as the proximal end of the branch graft is brought into approximation with the branch graft opening of the primary graft using a balloon through the primary graft, the snap connector member including a channel sized such that a proximal surface defining the channel contacts a proximal end of the port member and a distal surface defining the channel contacts the distal end of the port member, said engagement of the snap connector member to the port member being operative to form a connection between the branch graft and the primary graft, wherein the snap connector member further includes a tapered leading edge distal of the channel, wherein the tapered leading edge aids in a transition of the port member into the channel.

2. The system of claim 1, wherein the snap connector member further includes a flange proximal of the channel, wherein the flange is configured to conform to an interior of the primary graft.

3. The system of claim 1, wherein said primary graft is at least partially formed from materials selected from the group of materials comprising woven polyester, expanded polytetrafluoroethylene, and Dacron.

4. The system of claim 1, wherein said branch graft is at least partially formed from materials selected from the group of materials comprising woven polyester, expanded polytetrafluoroethylene, and Dacron.

5. The system of claim 1, wherein the port member is a ring element.

6. The system of claim 1, wherein the branch graft opening is formed on the side of the primary graft.

* * * * *